United States Patent
Wells et al.

(10) Patent No.: US 10,006,891 B2
(45) Date of Patent: Jun. 26, 2018

(54) ANALYTICAL INSTRUMENTATION, ANALYTICAL INSTRUMENT ASSEMBLIES, AND ANALYTICAL METHODS

(75) Inventors: James Mitchell Wells, Lafayette, IN (US); Mark Gregory, Lafayette, IN (US); Matt Briscoe, Zionsville, IN (US)

(73) Assignee: FLIR Detection, Inc., Stillwater, OK (US)

(*) Notice: Subject to any disclaimer, the term of this patent is extended or adjusted under 35 U.S.C. 154(b) by 59 days.

(21) Appl. No.: 12/952,495

(22) Filed: Nov. 23, 2010

(65) Prior Publication Data

US 2011/0146381 A1    Jun. 23, 2011

Related U.S. Application Data

(60) Provisional application No. 61/264,547, filed on Nov. 25, 2009.

(51) Int. Cl.
| | |
|---|---|
| *G01N 30/04* | (2006.01) |
| *G01N 30/72* | (2006.01) |
| *G01N 30/20* | (2006.01) |

(52) U.S. Cl.
CPC ......... *G01N 30/7206* (2013.01); *G01N 30/20* (2013.01)

(58) Field of Classification Search
CPC ...... G01N 1/2247; G01N 1/22; G01N 1/2273; G01N 30/20; G01N 30/7206; G08B 21/14
USPC .............. 73/61.52, 61.55, 23.22, 863.31
See application file for complete search history.

(56) References Cited

U.S. PATENT DOCUMENTS

| | | | | |
|---|---|---|---|---|
| 4,856,352 | A * | 8/1989 | Daum et al. ............... | 73/863.25 |
| 5,281,256 | A * | 1/1994 | Sacks et al. ...................... | 95/86 |
| 5,369,981 | A * | 12/1994 | Merz et al. .................. | 73/28.01 |
| 6,165,251 | A | 12/2000 | Lemieux et al. | |
| 6,477,906 | B1 * | 11/2002 | Peterson .................. | G01N 1/26 |
| | | | | 73/31.02 |
| 6,649,129 | B1 | 1/2003 | Neal | |
| 7,135,056 | B2 * | 11/2006 | Henderson ........................ | 95/82 |

(Continued)

FOREIGN PATENT DOCUMENTS

EP    2 362 215    8/2011

OTHER PUBLICATIONS

Camel et al., "Trace Enrichment Methods for the Determination of Organic Pollutants in Ambient Air" J. Chrom. A., 710 (1995) 3-19.

*Primary Examiner* — Helen Kwok
*Assistant Examiner* — Nashmiya Fayyaz
(74) *Attorney, Agent, or Firm* — Wells St. John P.S.

(57) ABSTRACT

Analytical instruments are provided that can include a sample inlet component with the sample inlet component including a first sampling port; a plurality of sample capturing assemblies; and a first valve assembly in fluid communication with both the sampling port and the sample capturing assemblies. The instrument can further include a sample analysis component in fluid communication with the first valve assembly of the sample inlet component; and an instrument control component in controlling communication with both the sample inlet component and the analysis component. Instrumental analysis methods are provided that can include continuously providing sample to at least one of a plurality of sample capturing assemblies; and selectively analyzing the contents of at least one of the plurality of sample capturing assemblies.

3 Claims, 15 Drawing Sheets

(56) References Cited

U.S. PATENT DOCUMENTS

| | | |
|---|---|---|
| 7,600,439 B1 | 10/2009 | Patterson et al. |
| 7,637,147 B2 * | 12/2009 | Lee et al. .................... 73/61.56 |
| 2005/0092109 A1 * | 5/2005 | Albro et al. ............... 73/863.83 |
| 2005/0252859 A1 * | 11/2005 | Hofmann et al. ............ 210/656 |
| 2008/0121016 A1 * | 5/2008 | Shah et al. ................... 73/23.42 |
| 2011/0016951 A1 * | 1/2011 | Reuter ........................ 73/23.42 |

* cited by examiner

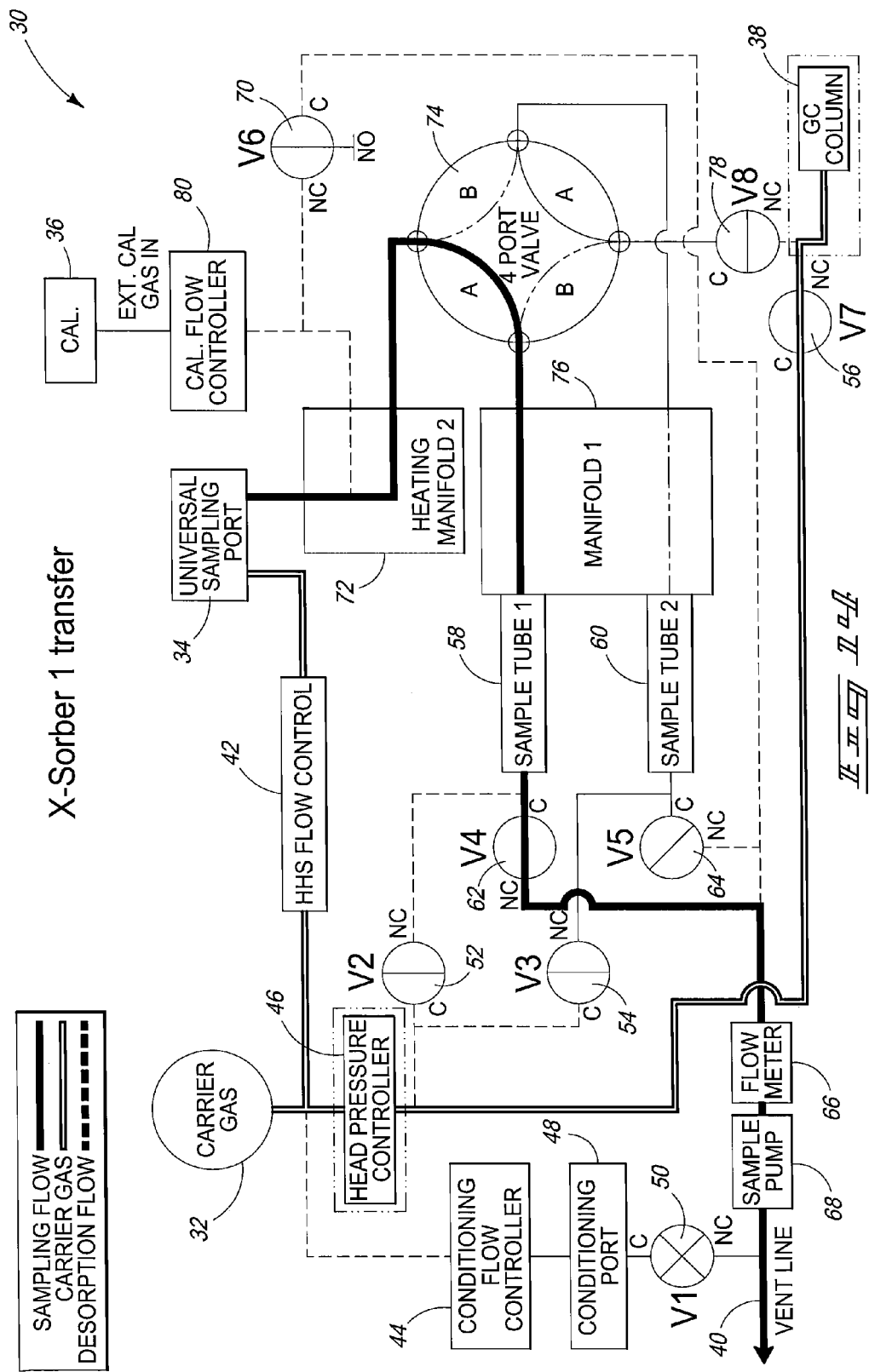

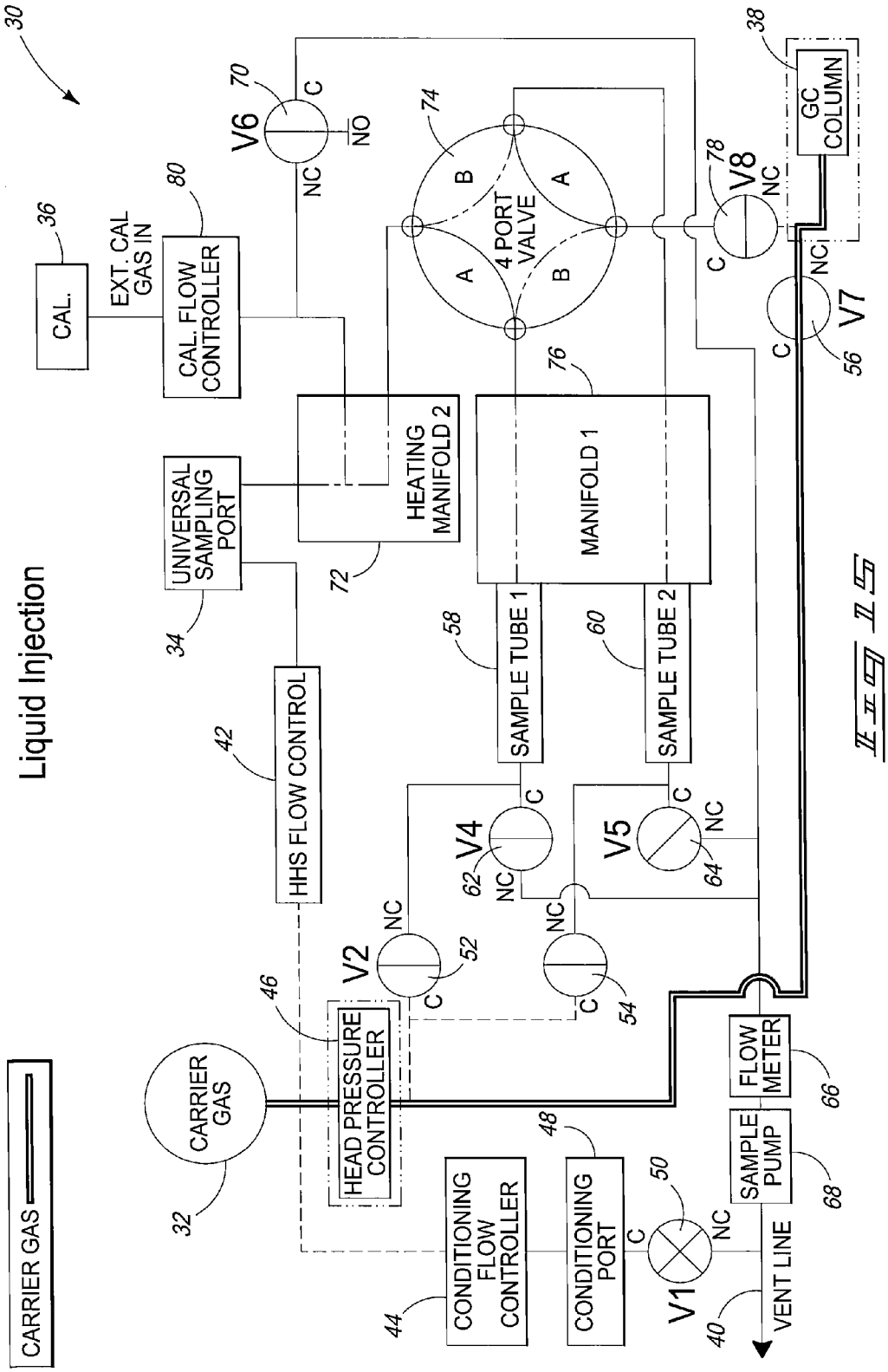

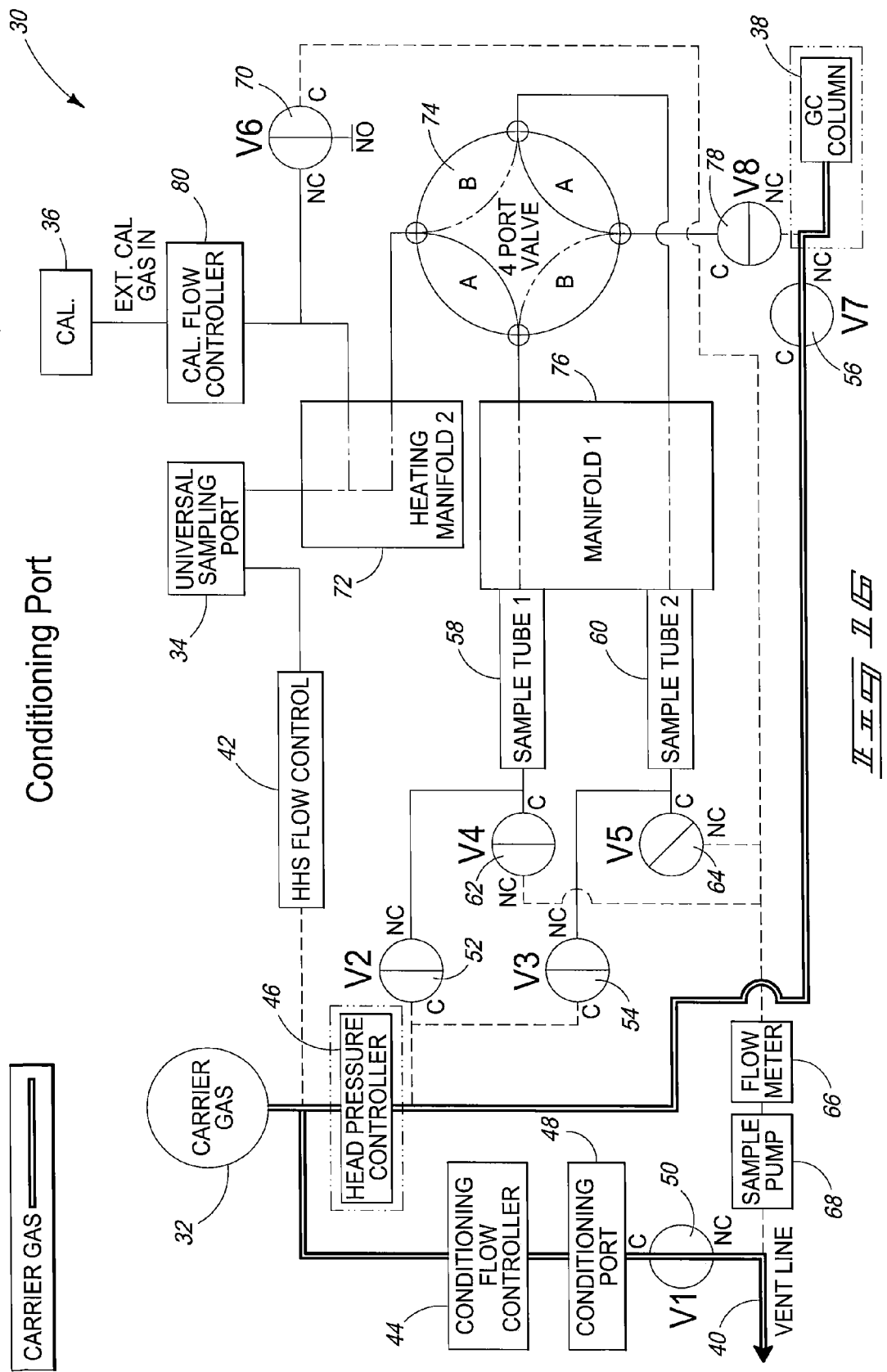

ANALYTICAL INSTRUMENTATION, ANALYTICAL INSTRUMENT ASSEMBLIES, AND ANALYTICAL METHODS

CROSS REFERENCE TO RELATED APPLICATION

This application claims priority to U.S. Provisional Patent Application No. 61/264,547 which was filed on Nov. 25, 2009, the entirety of which is incorporated by reference herein.

TECHNICAL FIELD

The present disclosure relates to the area of instrumental analysis and more particularly to the field of analytical instrumentation. Embodiments of the present disclosure relate to analytical assemblies and/or methods as well air sampling and gas chromatography/mass spectrometry (GC/MS) assemblies and methods.

BACKGROUND

Analytical instrumentation has been utilized to characterize the constituents of samples for decades. Problems with this instrumentation have occurred when more than one type of sample, continuous sampling, and multiple types of analyses have been attempted utilizing limited instrumentation. Instruments have failed to allow the operator to perform one type of sampling as well as preparing to perform another type of sampling analysis with the same instrument.

In particular, GC/MS has been utilized to yield a very high degree of chemical information from few sample analyses. GC/MS can be used to confirm sample characteristics as well as component identification. Having this ability can be very desirable for some applications, such as building protection, where a large number of people could be affected by chemical/munitions attack. Misidentification in these situations can lead to large expenses in terms of time, money, and lost productivity.

The present disclosure provides instrumentation and sampling methods that allow the user to perform multiple analysis and multiple sampling techniques utilizing the same instrumentation.

BRIEF DESCRIPTION OF THE DRAWINGS

Preferred embodiments of the disclosure are described below with reference to the following accompanying drawings.

FIG. 13 is another configuration of the instrument of FIG. 3 according to an embodiment.

FIG. 14 is another configuration of the instrument of FIG. 3 according to an embodiment.

FIG. 15 is another configuration of the instrument of FIG. 3 according to an embodiment.

FIG. 16 another configuration of the instrument of FIG. 3 according to an embodiment.

DESCRIPTION

This disclosure is submitted in furtherance of the constitutional purposes of the U.S. Patent Laws "to promote the progress of science and useful arts" (Article 1, Section 8).

The instruments, assemblies, and methods will be described with reference to FIG. 1-16. Embodiments of the instruments, assemblies and/or methods described can provide mobile, integrated GC/MS systems with continuous air sampling capability for example. Embodiments of the disclosure can provide rapid introduction of ambient air (and/or other gas-phase samples) to the mobile gas GC/MS for determination of potentially hazardous compounds in the air. Aspects of embodiments of the disclosure can provide the capability to continuously sample air, with no interruption in the sampling. Such interruptions are obviously undesirable as they could lead to the missed detection of a transient chemical threat in the air.

Continuous sampling can be accomplished by using multiple sampling sorbent tubes (two at a minimum, but more are contemplated) connected to appropriate valves and flow controllers in such a way that the sample flow into the instrument can be directed into one tube to trap compounds from an air sample, while another tube's trapped constituents are being analyzed by the GC/MS. After a tube is analyzed, cooled, and ready to take another sample, the valves can be switched so that the sample is directed onto the ready tube, and the tube that has been sampling is analyzed by the GC/MS.

To support the analysis of a wide possible variety of analytical samples, the embodiments of the instruments, assemblies, and/or methods can provide the capability to accept/introduce liquid samples which are typically introduced to a heated GC injector with a syringe. Solid samples can be analyzed as well, and in this case, the solid is dissolved in common solvents amenable to GC use. Embodiments of the instruments, assemblies, and/or methods can also be used to analyze samples collected via solid phase micro-extraction (SPME), purge-and-trap systems, head space systems, hand-held air samplers and thermal desorbers such as the Griffin X-Sorber™ and a variety of other sample collection methods known in the art of analytical instrumentation.

Figure 1:
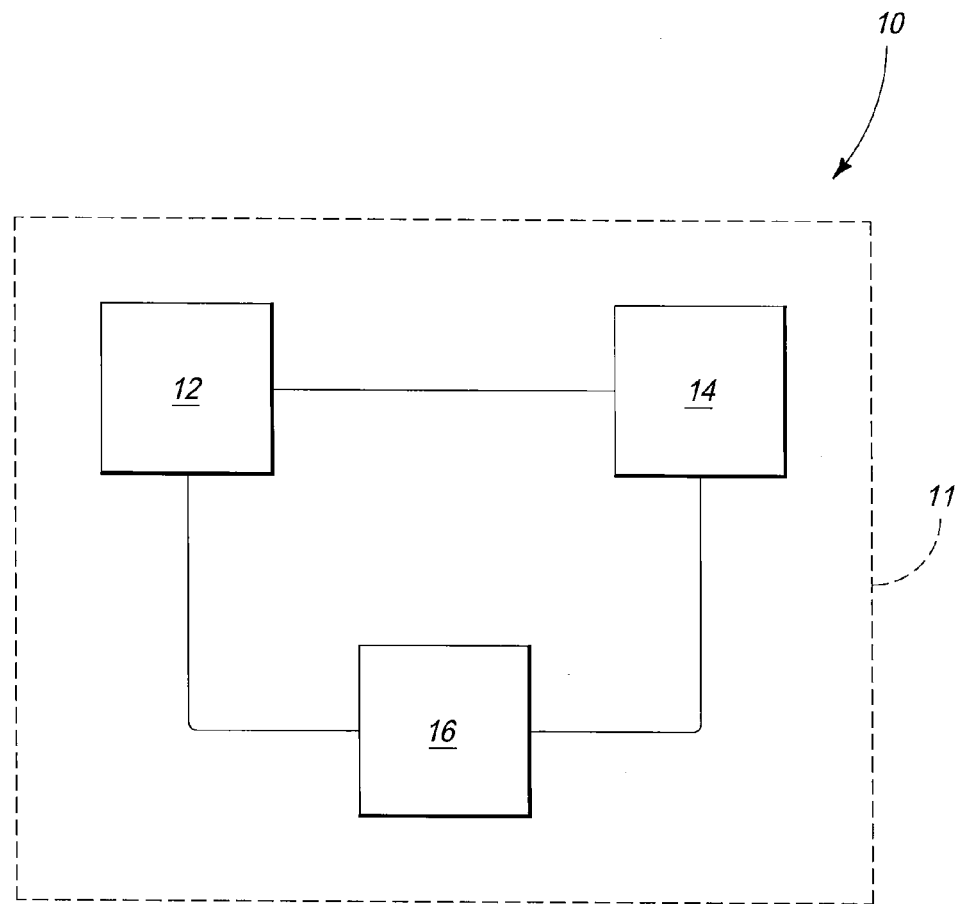
FIG. 1 is an instrument according to an embodiment.

Referring first to FIG. 1, an analytical instrument 10 is provided that includes a housing 11 encompassing a sample inlet component 12 coupled to a sample analysis and/or detection component 14, both of which are coupled to an instrument control and/or data analysis processing component 16. Component 14 can be in fluid communication with at least a portion of inlet component 12. Component 16 can be in controlling communication with both inlet component 12 and analysis component 16. Component 14 can include an analyte modification component and a detection component, either or both of which may be coupled to processing component 16 which can include processing circuitry and/or storage circuitry. Instrument 10 may include a sample inlet component 12 configured to receive sample and convey sample to an analyte modification component. Instrument 10 can also include a detection component and processing circuitry that may be coupled to one or more of sample inlet component 12, analyte modification component, detection component, and/or storage circuitry. Housing 11 can define the housing of the instrument. The housing can be a framed shell that defines a volume occupied by the instrument. The housing itself can encompass the entirety of the instrument 10.

Sample can be introduced into sample inlet component 12. Sample inlet component 12 can be configured to introduce an amount of sample into component 14 for analysis. Depending upon the sample, sample inlet component 12 may be configured to prepare the sample for introduction into components such as analyte modification components and detection components. Component 12 can include a sampling port and this sampling port may be coupled to additional sample inlets such as but not limited to batch inlets, direct probe inlets, chromatographic inlets, and permeable, semi-permeable, solid phase micro extractions (SPME) and/or capillary membrane inlets. Sample inlet component 12 can also be configured to prepare the sample for analysis in the gas, liquid and/or solid phase. Sample inlet component 12 can be configured to provide the sample according to sample inlet parameters stored and/or dictated by component 16.

Sample inlet component 12 can be configured to provide the sample to component 14 according to multiple configurations. For example sample inlet component 12 can be configured as a continuous air sampler to acquire a first data set in one instance and configured as a gas chromatograph inlet to acquire a second data set in another instance. In an example embodiment, sample inlet component 12 can be a chromatographic inlet and the sample inlet parameter of the chromatographic inlet can be a parameter than influences elution of the sample or portions of the sample from the chromatographic inlet. In one aspect, where the chromatographic inlet is a gas chromatographic inlet, an example sample inlet parameter can include the temperature value of a chromatography column of the gas chromatographic inlet. In some configurations, sample inlet component 12 may be combined with the analyte modification component.

Figure 2:
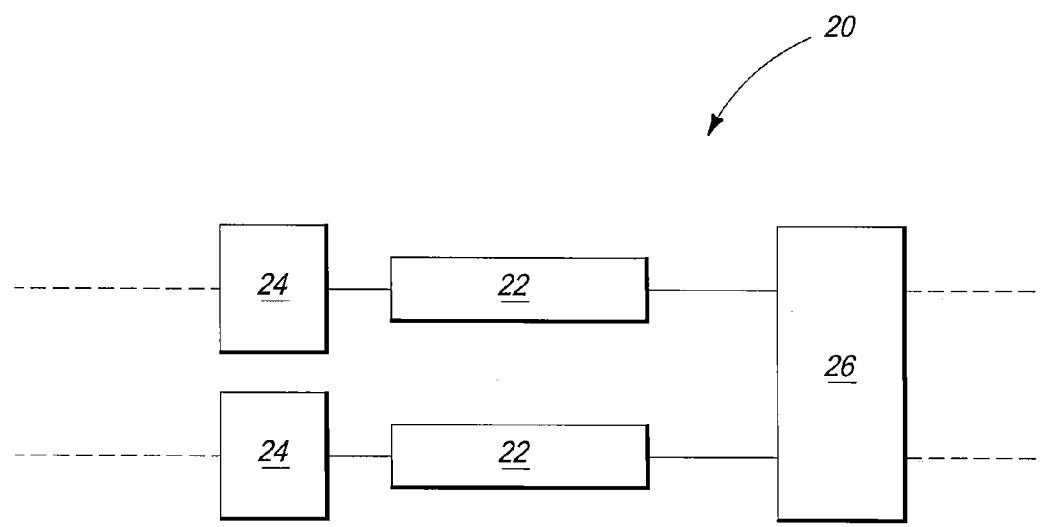
FIG. 2 is an assembly of an instrument according to an embodiment.

Referring to FIG. 2, component 12 can include an assembly 20. Assembly 20 can include a plurality of sample capturing assemblies 22 each in fluid communication with valves assemblies 24 and 26. Assemblies 22 are depicted as serially aligned. As shown, valve assemblies 24 can include multiport 2-way valves individually associated with individual assemblies 22. It is contemplated that valve assemblies 24 can be replaced with a single multiport 4-way valve coupled to multiple assemblies 22, such as two assemblies 22. Assemblies 22 can also be in fluid communication with a multiport 4-way valve assembly such as valve assembly 26. It is contemplated that the multiport 4-way valve assembly 26 can be replaced by two independent multiport 2-way valve assemblies. As an example, component 12 can include at least two assemblies 22 and each of these assemblies may be in fluid communication with a different port of multiport 4-way valve assembly 26. In accordance with example implementations, assembly 26 can be in fluid communication with a sampling port of component 12, and/or both valve assemblies can be in fluid communication with one another via one or more of assemblies 22.

Figure 3:
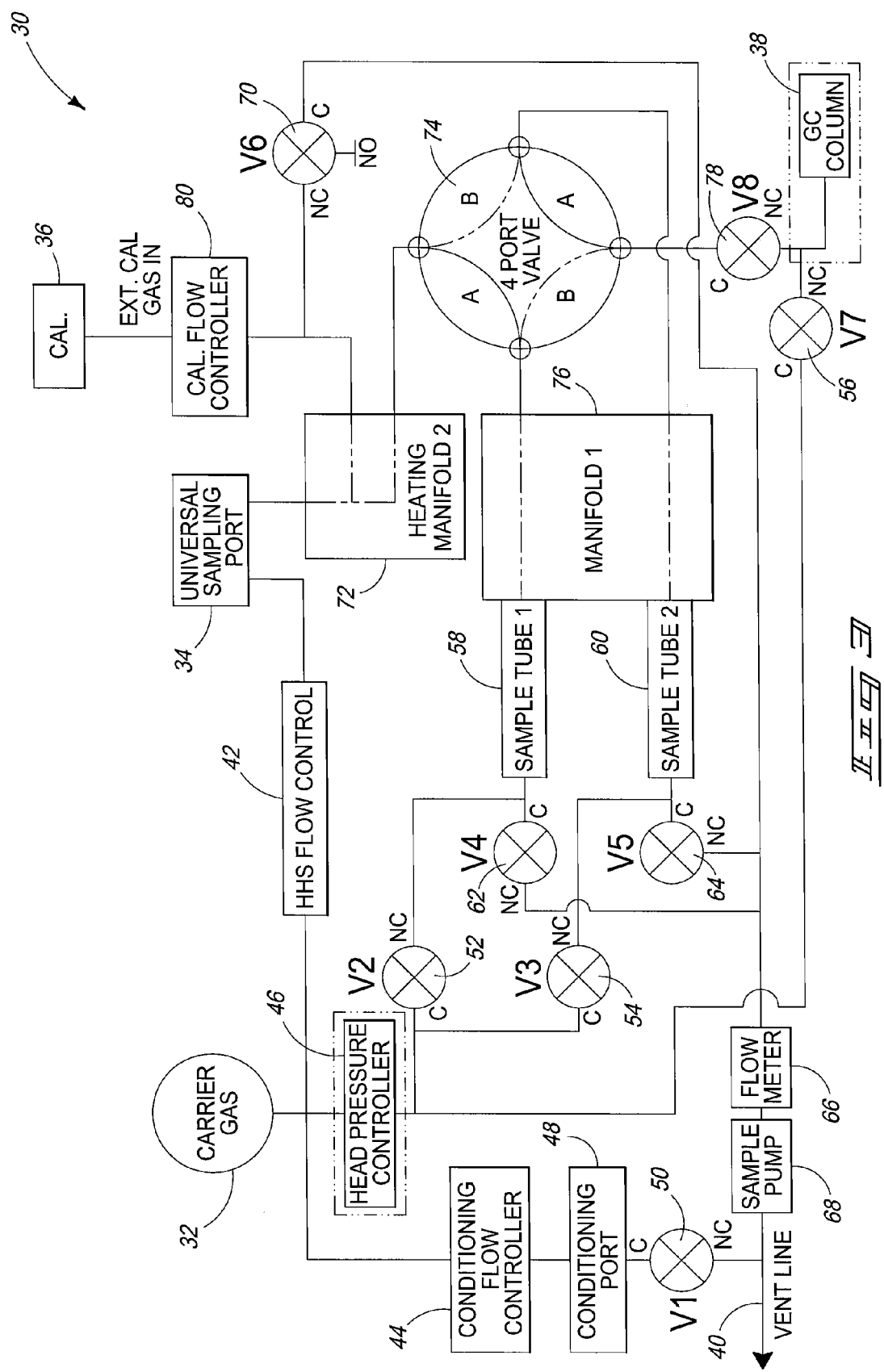
FIG. 3 is a configuration of an instrument according to an embodiment.

According to an example embodiment, instrument 10 can include a sample inlet component 12 and this component 12 can include a sample inlet port such as universal sampling port 34 of FIG. 3. Component 12 can also include sample capturing assemblies 22 as well as a first valve assembly 26 in fluid communication with both the sample inlet port and assemblies 22. A sampling port of component 12 can be configured to continuously draw atmosphere from a predefined sample acquisition point. This acquisition point can be a mobile or stationary point as instrument 10 may be used while being transported or in a fixed position.

Assemblies 22 can include solid phase sorbent materials for example. These materials can have a known affinity for analytes having a known chemistry and assemblies 22 may have the same or different sorbent materials therein. Assemblies 22 can be Sorbent tubes packed with a sorbent such as Tenax TA, Hayesep C, Carboxen 569, Carboxen 1017, and/or other sorbents or combinations of same. As an example, tubes with approximately 50% (wt./wt.) Tenax TA and 50% (wt./wt.) Carboxen 1017 may be utilized.

In example configurations, valve assemblies 24 can be in fluid communication with pressure differentiating apparatuses such as carrier gas supply or vacuum apparatuses. In these configurations, assemblies 24 can be selectively configured to provide either negative or positive pressure to assemblies 22. In accordance with one configuration, negative pressure may be provided to an individual assembly 22 while in fluid communication with a sampling port via assembly 24 to draw sample into assembly 22. In accordance with another configuration, positive pressure may be provided to an individual assembly 22 while in fluid communication with component 14 via assembly 24 to provide sample into component 14 for analysis. Valve assemblies 26 can be also be in fluid communication with a vent line and/or a carrier gas supply such as a pressurized carrier gas supply. Assemblies 22 may also be in fluid communication with additional 2-way valves that allow control of carrier gas to and through assemblies 22.

Referring to FIG. 3, an embodiment of component 12 as represented in FIG. 1 is shown as assembly 30. As shown, assembly 30 can include a system of valves, conduit, flow and head pressure controllers/meters, pumps, manifolds, and sampling preparation components. More particularly, assembly 30 can include the pressure differentiating apparatus as a carrier gas supply 32 coupled to the system as well as the sample port as a universal sampling port 34, and a calibrant 36 coupled to the system. The system is further coupled to analysis component 14 than can include a gas chromatography column 38 and the system also includes a vent 40 such as an evacuation conduit.

Carrier gas 32 can be coupled to two flow controllers, an HHS flow controller 42 and a conditioning and flow controller 44. Both these flow controllers can provide flow of carrier gas to head pressure controller 46, and these flow controls can provide at least part of the positive flow through system 30. Conditioning flow controller 44 can be coupled to, and in fluid communication with, conditioning port 48, which is also coupled to a 2-way valve 50 which allows control of flow to vent line 40.

Head pressure controller 46 can be in fluid communication with at least two valves, 2-way valve 52 and 2-way valve 54, which can be an embodiment of valve assemblies 24, for example. Controller 46 can also be in fluid communication with 2-way valve 56. Valves 52 and 54 can facilitate fluid communication between carrier gas 32 and sample capturing assemblies such as sample tubes 58 and 60, respectively. Valves 52 and 54 can also provide fluid communication between carrier gas and valves 62 and 64 as well. Valves 62 and 64 together or in combination with valves 52 and 54 can be an embodiment of valve assemblies 24, for example. Two-way valves 62 and 64 can be in fluid communication with both sampling tubes 58 and 60, for example, as well as in fluid communication with vent line 40 via flow meter 66 and sample pump 68. In accordance with example implementations, providing sample to at least one of the plurality of sample capturing assemblies can include drawing sample from the sample port to the at least one of the sample capturing assemblies. The sample can be drawn through valve assembly 74 to tube 58 for example, by engaging sample pump 68 and flow meter 66 to provide fluid communication between the at least one of the plurality of the sample capturing assemblies and a vacuum source. In accordance with the example configuration, a valve assembly such as assembly 24 of FIG. 2, or more specifically assembly 62 of FIG. 3 can be operated to provide fluid communication between the at least one of the plurality of the sample capturing assemblies and the vacuum source. Flow meter 66 can be utilized to control the flow from valve 70 as well.

Universal sampling port 34 can be in fluid communication with HHS flow control 42. Universal sampling port 34 can also be in fluid communication with heating manifold 72 which is in fluid communication with 4-port valve 74. Four-port valve 74 can be an embodiment of valve assembly 26, for example, and can be in fluid communication with both sampling tubes 58 and 60 via manifold 76 as well as 2-way valve 78. In accordance with example implementations, providing sample to sample capturing assemblies can include providing sample from the sample port such as port 34 via a valve assembly such as valve 74.

With respect to assembly 30, calibrant 36 can be in fluid communication with calibrant flow controller 80, which can be in fluid communication with 4-port valve 74 as well as 2-port valve 70.

Figure 4:
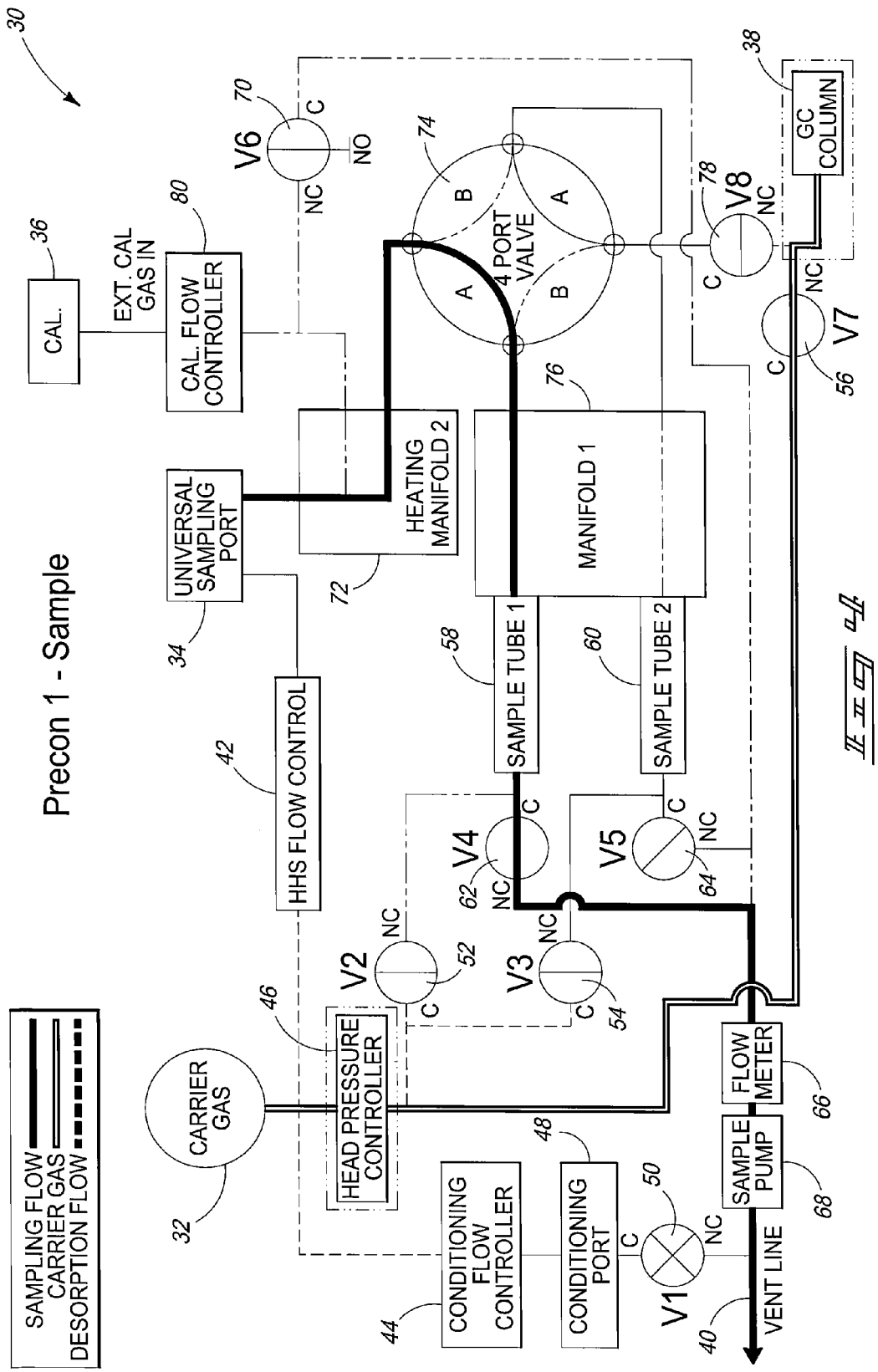
FIG. 4 is another configuration of the instrument of FIG. 3 according to an embodiment.

Referring to FIG. 4, assembly 30 is shown as configured in accordance with Table 1 below. Processing and control circuitry can be utilized to facilitate the configuration of assembly 30 via the manipulation and programming of the configuration of flow controllers and valves. Sample can be introduced via the universal sampling port and provided to sample tube 58 and analytes collected/concentrated therein for example.

In accordance with example implementations, a continuous sampling instrumental analysis method is provided. This method can include continuously providing sample to at least one of a plurality of sample capturing assemblies. Referring to FIG. 4, assembly 30 is configured to continuously provide sample from port 34 to tube 58, for example.

Also in accordance with example implementations, assembly 30 can be equipped with an additional sampling port in fluid communication with head pressure controller 46. This additional sampling port can be configured to receive liquid samples, for example. In this configuration, carrier gas can provide samples via this additional sampling port to GC column 38, which allows the user to perform gas chromatography if desired.

TABLE 1

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | Off | On | Off | Off | On | Off | A |

Figure 5:
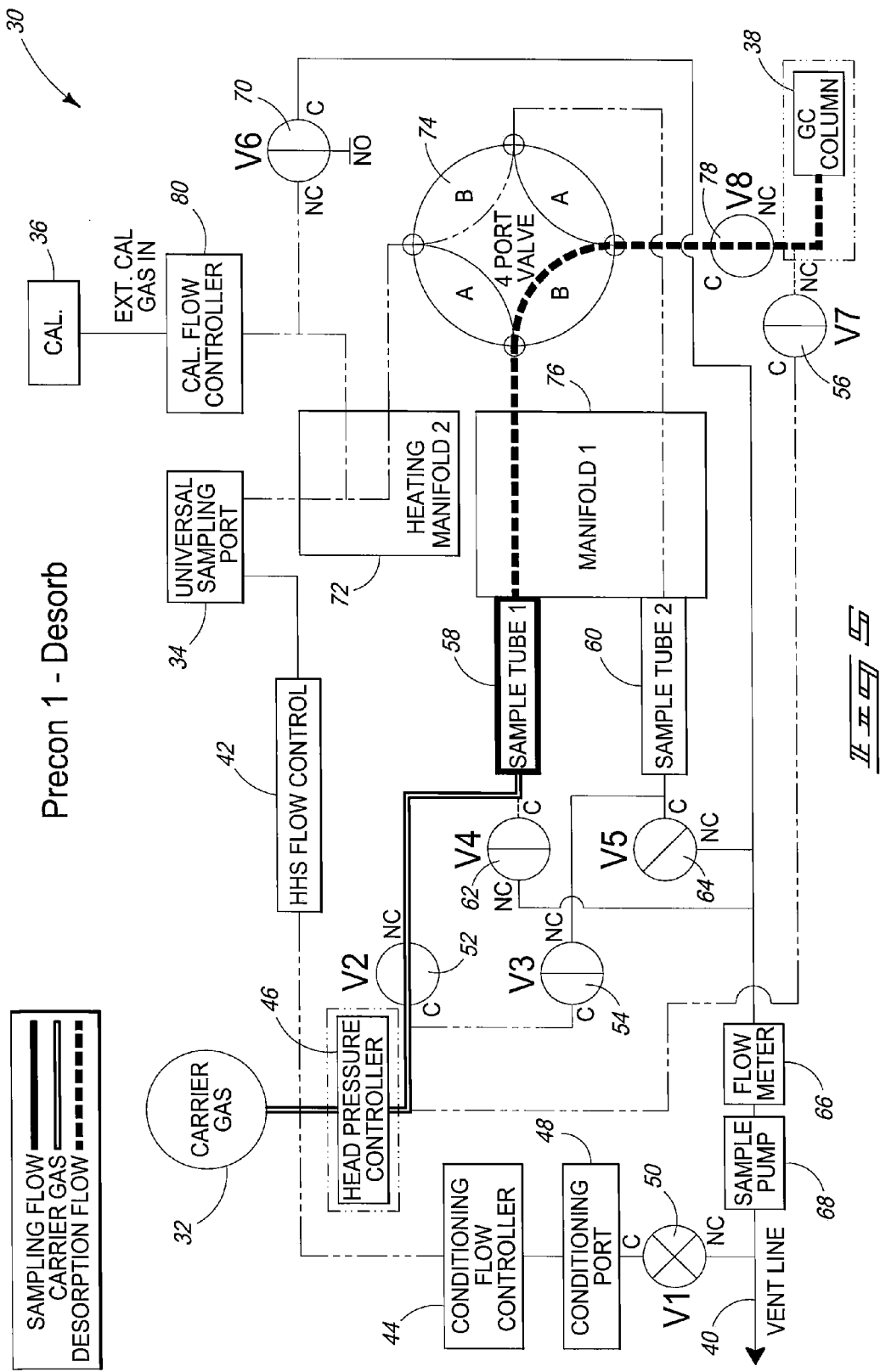
FIG. 5 is another configuration of the instrument of FIG. 3 according to an embodiment.

In accordance with example implementations, the contents of the at least one of the plurality of sample capturing assemblies can be selectively analyzed. For example, the contents of the at least one of the assemblies can be provided to a sample analysis component via a valve assembly in fluid communication with the sample analysis component. According to example configurations, fluid communication can be provided between the one assembly and a pressure differentiation apparatus such as a carrier gas source to provide positive pressure. This fluid communication can be provided by operating a valve assembly such as valve assembly 52 and 62 to provide carrier gas pressure to tube 58. Referring to FIG. 5, assembly 30 is shown as configured in accordance with Table 2 below. In accordance with this configuration, the contents of at least of one of the plurality of sample capturing assemblies can be analyzed. Analytes captured on tube 58 can be desorbed to column 38 of a sample analysis component. Conduit between tube 58 and column 38 can be heated.

TABLE 2

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | On | Off | Off | Off | Off | Off | On | B |

Figure 6:
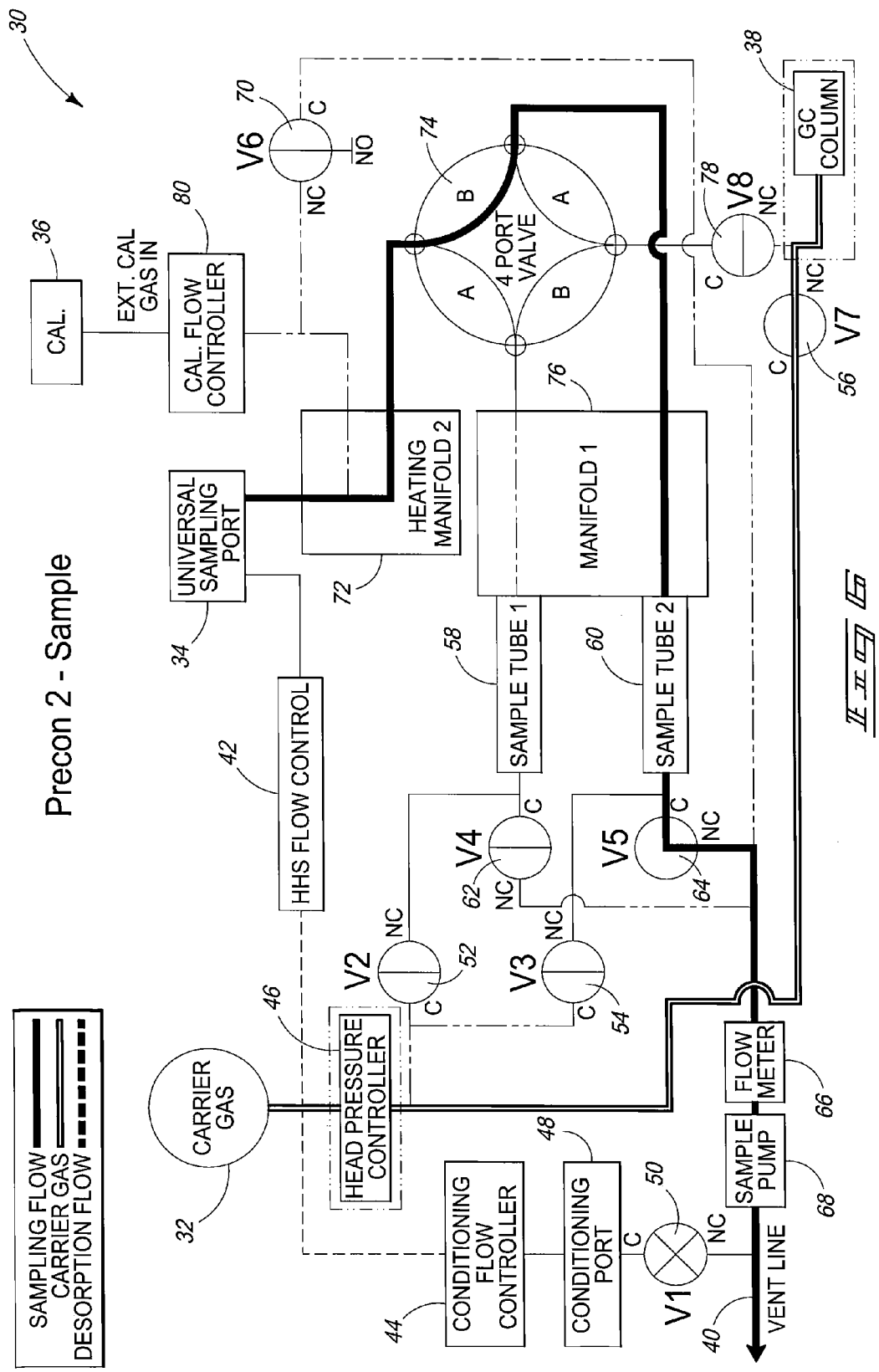
FIG. 6 is another configuration of the instrument of FIG. 3 according to an embodiment.

Referring to FIG. 6, assembly 30 is shown as configured in accordance with Table 3 below. Sample can be provided via universal sampling port 34 through 4-way valve 74 and on to tube 60 while carrier gas is provided to the GC column. In accordance with this configuration, sample can be provided to another of the plurality of sample capturing assemblies by drawing sample from the sampling port.

TABLE 3

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | Off | Off | On | Off | On | Off | B |

Figure 7:
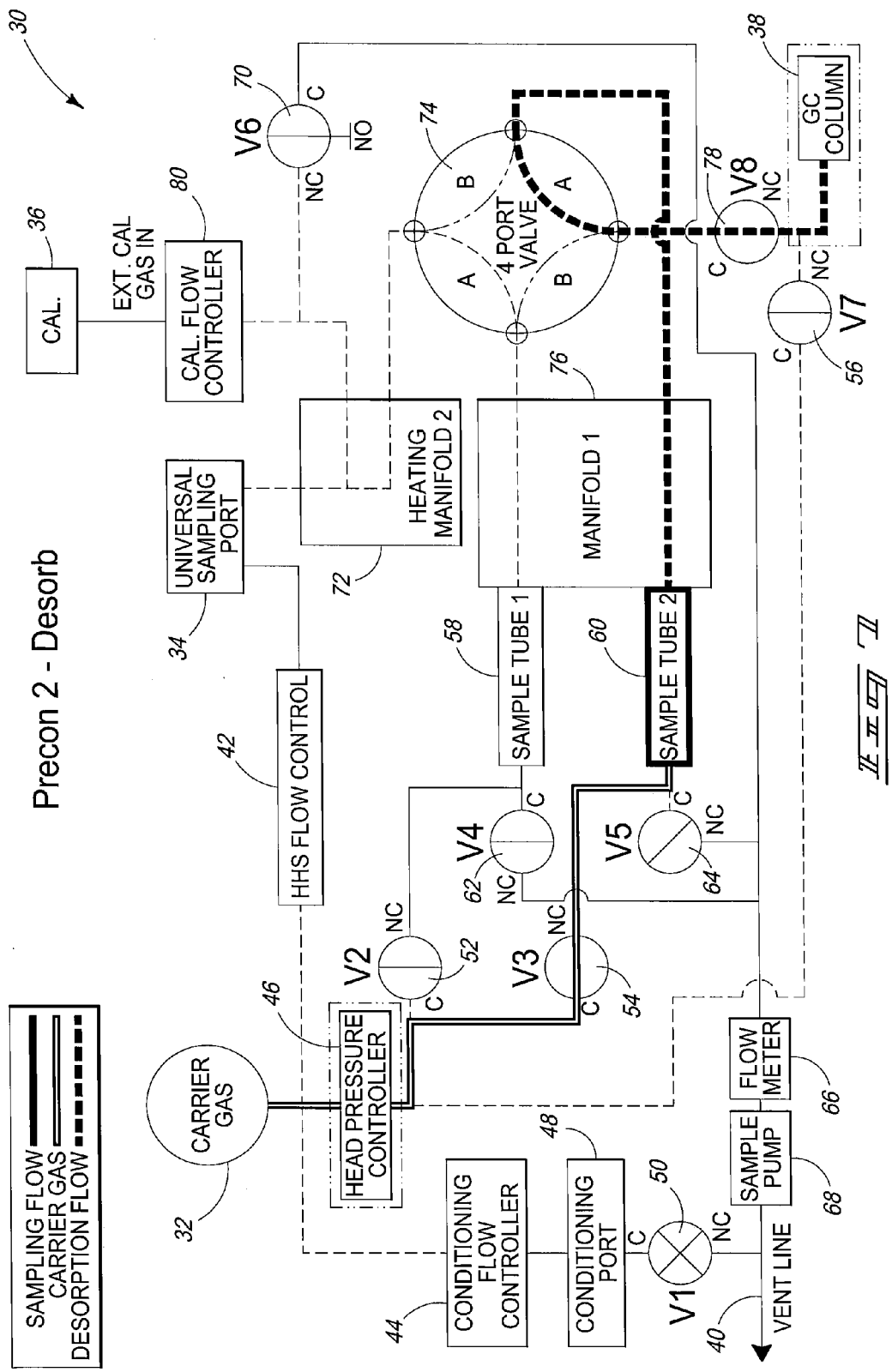
FIG. 7 is another configuration of the instrument of FIG. 3 according to an embodiment.

Referring to FIG. 7, assembly 30 is shown as configured in accordance with Table 4 below. As shown, analyte can be desorbed from tube 60 and provided to GC column 38. In accordance with this configuration, the contents of the other of the plurality of sample capturing assemblies can be provided to the sample analysis component by providing carrier gas pressure to the other assembly.

TABLE 4

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | On | Off | Off | Off | Off | On | A |

Figure 8:
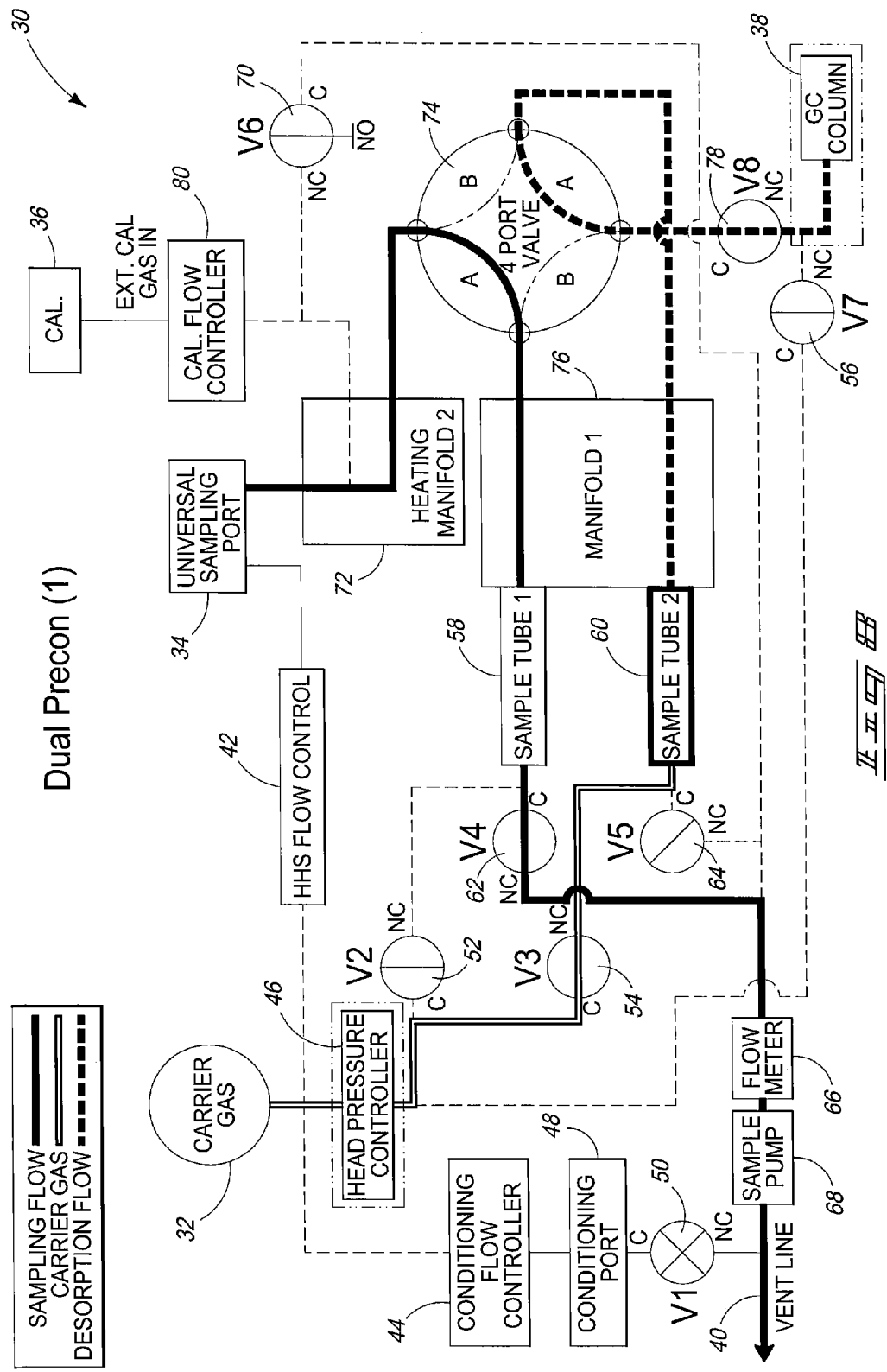
FIG. 8 is another configuration of the instrument of FIG. 3 according to an embodiment.

In accordance with an example embodiment, sample can be simultaneously provided to at least one of the sample capturing assemblies while the contents of another of the sample capturing assemblies is provided to the sample analysis component. Referring to FIG. 8, assembly 30 is shown as configured in accordance with Table 5 below. In this configuration, sample can be provided via universal sampling port 34 to tube 58, while simultaneously, analyte can be desorbed from tube 60 and provided to GC column 38. In accordance with this configuration assembly 30 is configured to simultaneously acquire/separate analyte from sample while simultaneously providing analyte from a previous acquisition/separation for further analysis. In this configuration, the instrumental analysis method can include selectively providing a vacuum source to continuously provide sample to the at least one of the plurality of the sample capturing assemblies, and selectively providing a carrier gas source to analyze the contents of at least one of the plurality of the sample capturing assemblies.

TABLE 5

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | On | On | Off | Off | Off | On | A |

Figure 9:
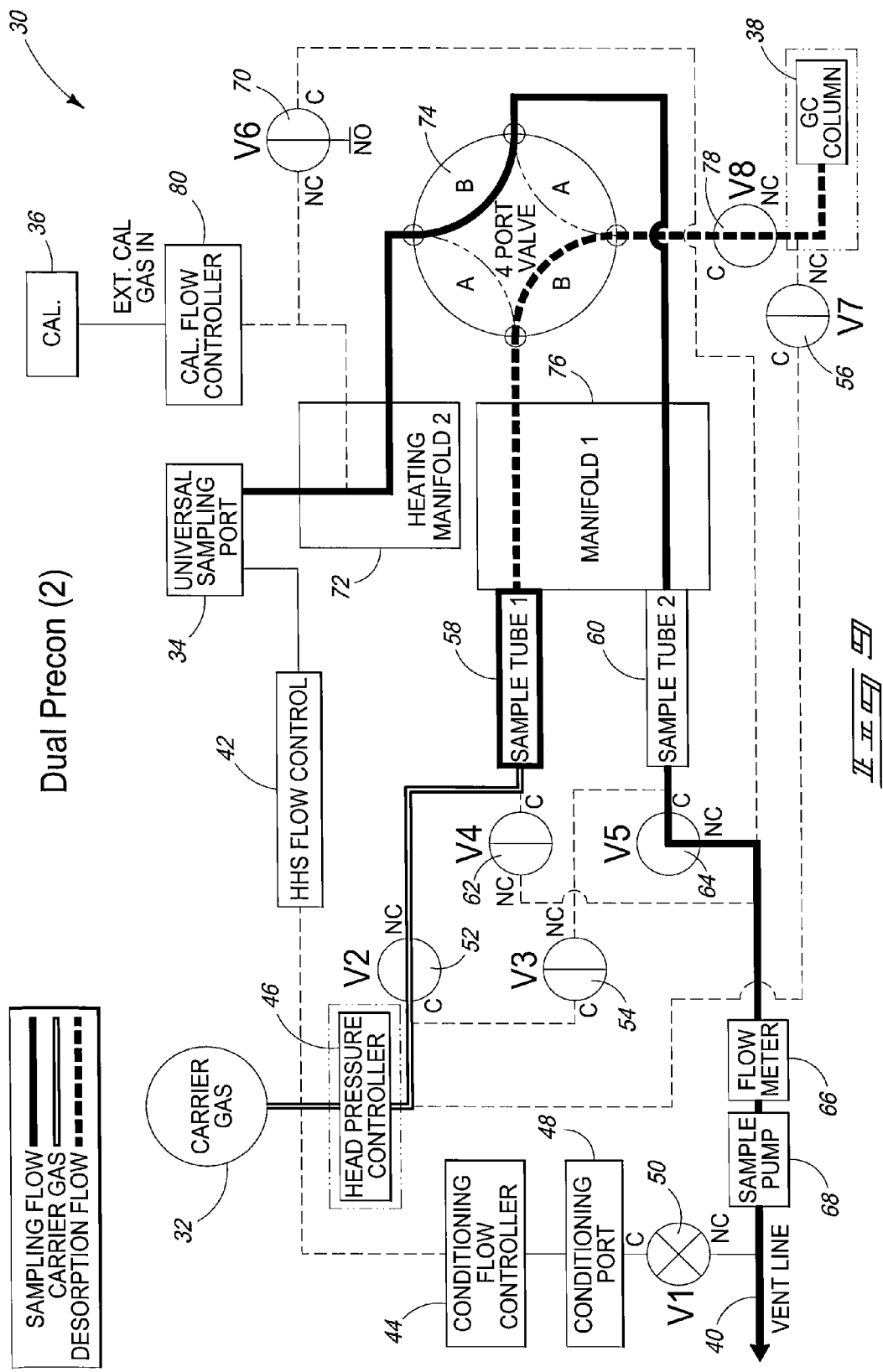
FIG. 9 is another configuration of the instrument of FIG. 3 according to an embodiment.

In accordance with example implementations, instrument 10 can be reconfigured to draw sample on the other of the sample capturing assemblies while simultaneously providing the contents of the one sample capturing assembly to the sample analysis component. Referring to FIG. 9, for example, assembly 30 is shown as configured in accordance with Table 6 below. In this configuration, sample can be provided via universal sampling port 34 to tube 60, while at the same time analyte previously acquired/separated in from tube 58 can be desorbed and passed to GC column 38 of the sample analysis component.

In accordance with example implementations, sample can be continuously analyzed by continuously providing sample to at least one of a plurality of sample capturing assemblies, and then analyzing the contents of the assemblies. Upon analysis of the contents of the sample capturing assemblies, the assembly can be preconditioned in preparation to receive yet more sample from the sample port. Thus, while instrument 10 is depicted with two sample capturing assemblies, another embodiment, not shown, can include at least three, with one of the three receiving sample, two of the three providing sample, and a third of the three being conditioned to receive sample.

TABLE 6

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | On | Off | Off | On | Off | Off | On | B |

Figure 10:
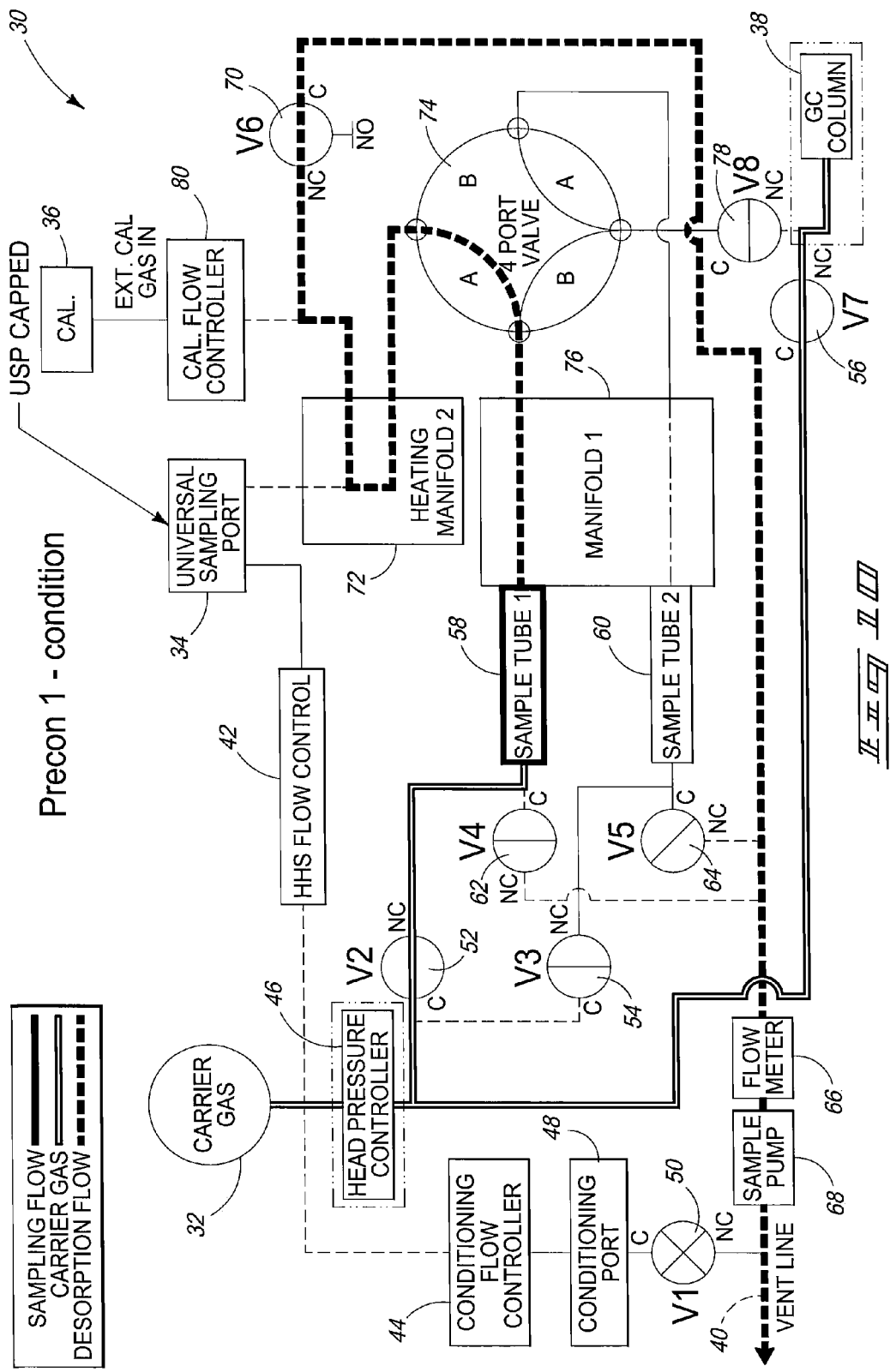
FIG. 10 is another configuration of the instrument of FIG. 3 according to an embodiment.

Referring to FIG. 10, assembly 30 is shown as configured in accordance with Table 7 below. Assembly 30 can be configured to precondition for sample introduction. Universal sampling port 34 can be capped, thereby not allowing sample to be provided there through. Head pressure can be provided from carrier gas to tube 58 and then exit via vent line 40. In this same configuration, carrier gas can be maintained to the front of GC column 38.

TABLE 7

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | On | Off | Off | Off | On | On | Off | A |

Figure 11:
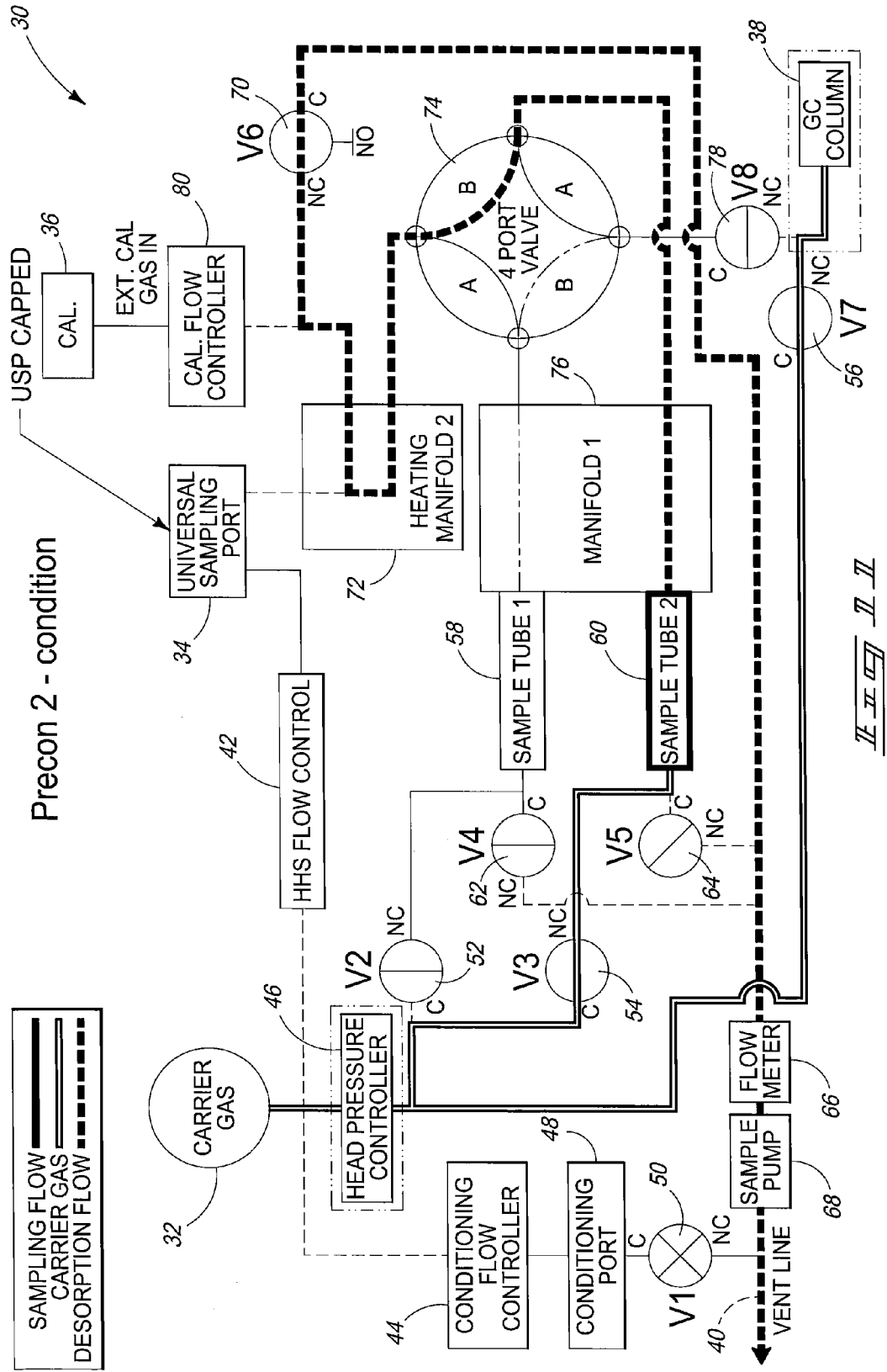
FIG. 11 is another configuration of the instrument of FIG. 3 according to an embodiment.

Referring to FIG. 11, assembly 30 is shown as configured in accordance with Table 8 below. In this configuration of assembly 30, tube 60 can be preconditioned utilizing a capped universal sampling port 34 and providing carrier gas via tube 60 through the 4-way valve and around to vent while maintaining head pressure to GC column 38.

TABLE 8

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | On | Off | Off | On | On | Off | B |

Figure 12:
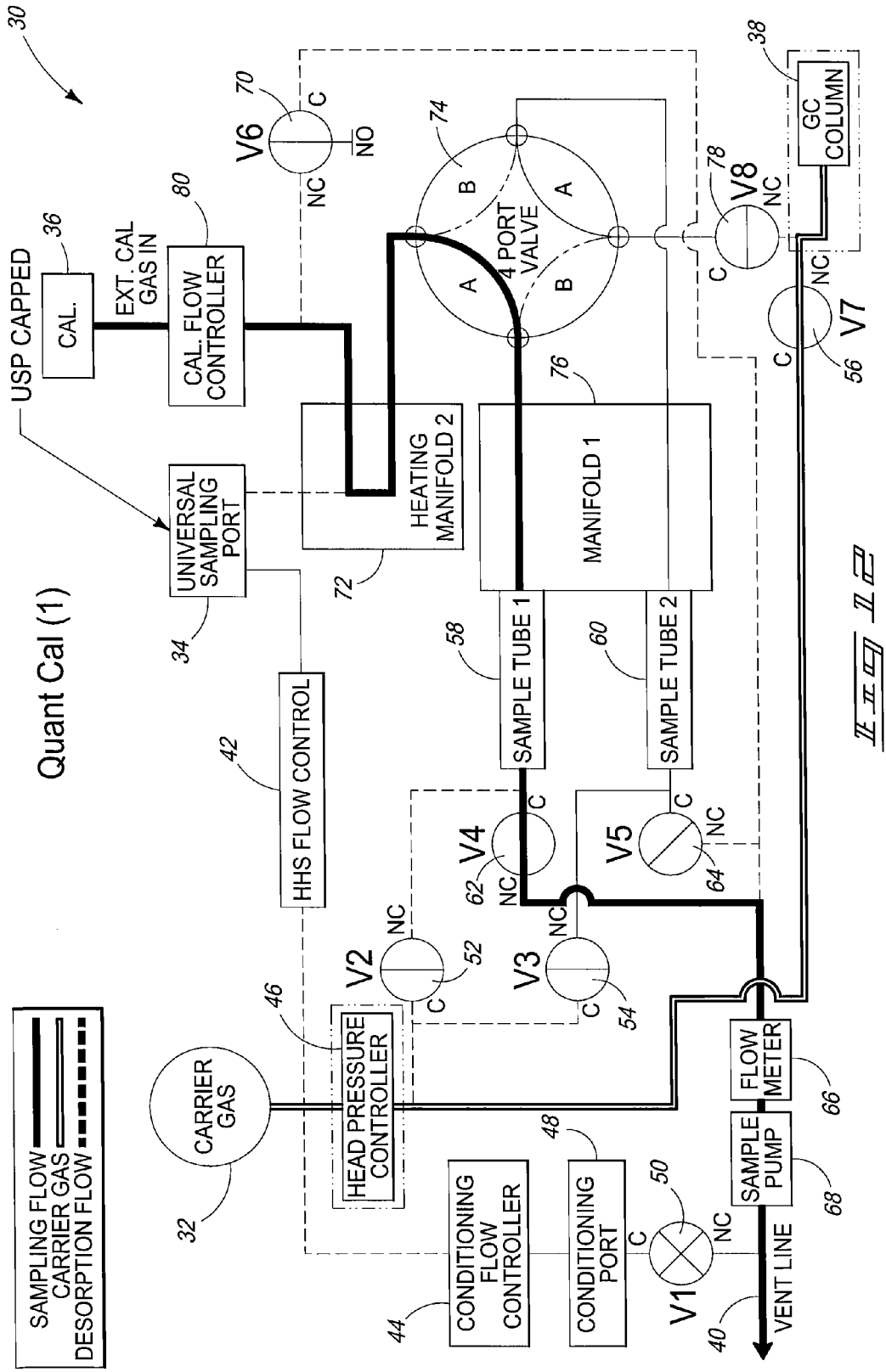
FIG. 12 is another configuration of the instrument of FIG. 3 according to an embodiment.
Figure 11:
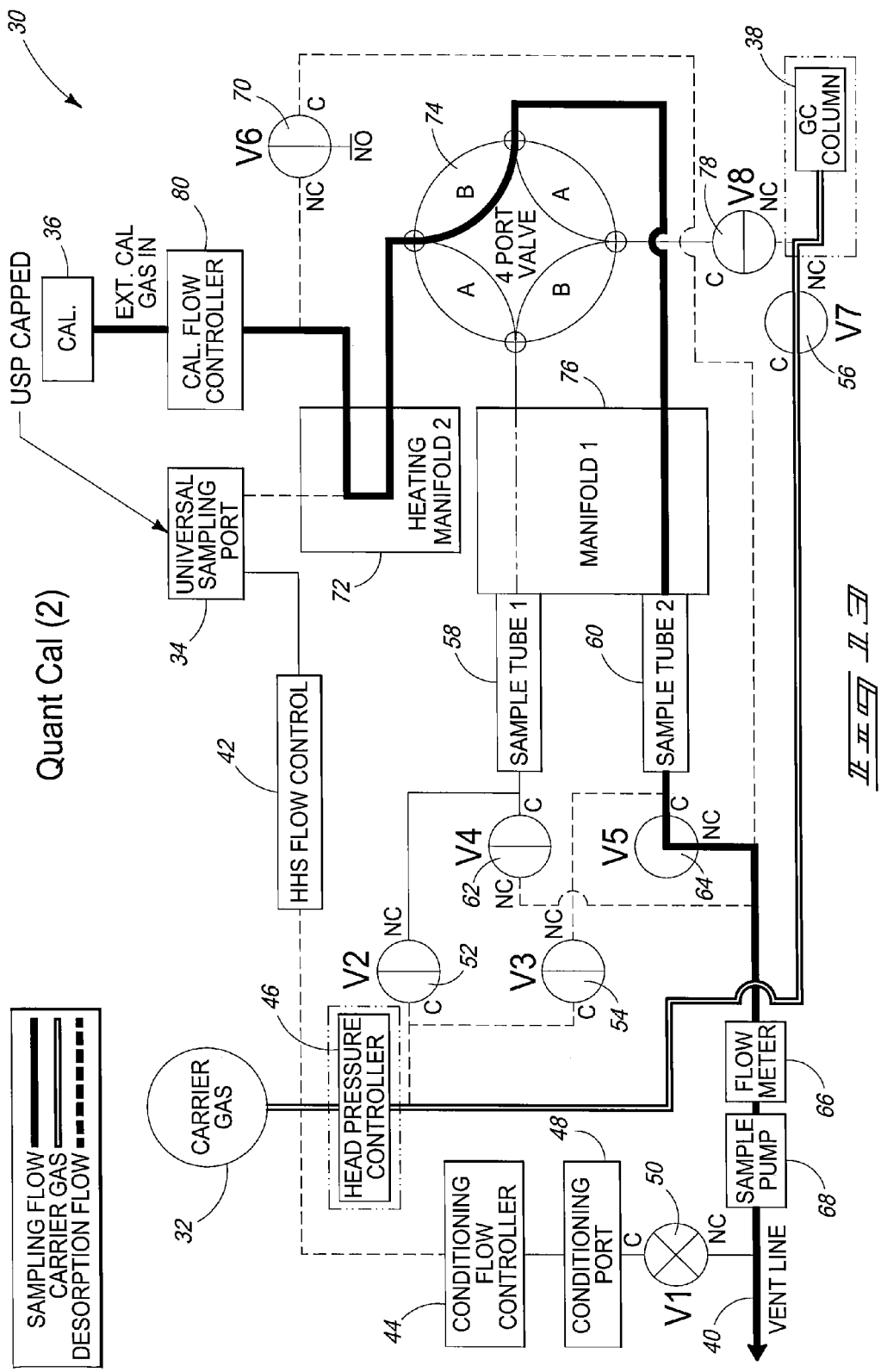

Referring to FIG. 12, assembly 30 is shown as configured in accordance with Table 9 below. Assembly 30 can be configured to provide a calibrant to instrument 10. As shown, universal sampling port 34 is capped, and calibrant 36 can be provided to tube 58. Carrier gas can be maintained to GC column 38.

TABLE 9

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | Off | On | Off | Off | On | Off | A |

Referring to FIG. 13, assembly 30 is shown as configured in accordance with Table 10 below. Calibrant 36 can be provided to tube 60 and utilized to calibrate instrument 10.

TABLE 10

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | Off | Off | On | Off | On | Off | B |

Referring to FIG. 14, assembly 30 is shown as configured in accordance with Table 11 below. In this configuration, other components can be coupled to assembly 30 and thus coupled to instrument 10. Sample and/or analyte from these other components can be provided to assembly 30 and also instrument 10. In accordance with example configurations, carrier gas 32 can also be directed via control 42 to USP 34 to these other components

TABLE 11

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | Off | On | Off | Off | On | Off | A |

Referring to FIG. 15, assembly 30 is shown as configured in accordance with Table 12 below. Assembly 30 can be configured for liquid injection of sample. As shown, carrier gas is provided to GC column 38 and sample can be provided via carrier gas entrance to head pressure control of component 30. SPME may be utilized to generate the liquid sample as well.

TABLE 12

| Valve 1 | Valve 2 | Valve 3 | Valve 4 | Valve 5 | Valve 6 | Valve 7 | Valve 8 | 4-port valve |
|---|---|---|---|---|---|---|---|---|
| On or Off | Off | Off | Off | Off | Off | On | Off | A or B |

Referring to FIG. 16, assembly 30 is shown as configured in accordance with Table 13 below. Assembly 30 can be configured to condition an external device such as a handheld adsorber. Carrier gas can be provided to conditioning flow controller and conditioning port and vented via valve to vent line, while at the same time maintaining head pressure to GC column 38.

TABLE 13

| Valve 1 | Valve 2 | Valve 3 | Valve 4 | Valve 5 | Valve 6 | Valve 7 | Valve 8 | 4-port valve |
|---|---|---|---|---|---|---|---|---|
| On | Off | Off | Off | Off | Off | On | Off | A or B |

Referring again to FIG. 1, analyte modification components of component 14 can be configured in exemplary embodiments to receive sample from sample inlet component 12, such as from GC column 38 of assembly 30, for example. Analyte modification component can be any component configured to modify an analyte upon exposure of the analyte to the analyte modification component. For example, the analyte modification component can be configured as an ionization component to process/ionize sample according to one or more parameters to form ionized analytes. In this configuration, analyte modification component parameters include ionization parameters that can include parameters that affect one or more of the amount of ionization, dissociation, and/or fragmentation of the sample when exposed to the analyte modification component. In an embodiment the analyte modification component can be configured to provide first and second ionization parameter values. The formation of ionized analytes from the sample can include the bombardment of the sample with electrons, ions, molecules and/or photons. The formation of ionized analytes within the analyte modification component can also be preformed by thermal or electrical energy according to the ionization parameter and its value.

The analyte modification component may be configured as, for example, an electron ionization component (EI, typically suitable for gas phase ionization), a photo ionization component (PI), a chemical ionization component, collisionally activated dissociation component (CID), electrospray ionization (ESI), and/or Flame Ionization. Other configurations are contemplated including analyte derivitisation components such as chemical derivitisation components for use in combination with gas chromatography and liquid chromatography. Furthermore, embodiments are contemplated that include the analyte modification component configured as multiple components such as both an electron impact ionization source and a chemical ionization source. Other contemplated embodiments include acquiring a data set with the analyte modification component configured in one configuration and acquiring another data set with the analyte modification component in another configuration. For example a data set can be acquired with the analyte modification component configured as electron ionization component and another data set can be acquired with the analyte modification component configured as chemical ionization component.

The analyte modification component can include a mass separation component as well. This mass separation component can include, but is not limited to ion trap, quadropole, time of flight, and/or ion mobility separation.

Analytes modified in the analyte modification component can be detected in the detection component. Exemplary detection components include electron multipliers, Farady cup collectors, photographic, scintillation-type detectors, UV, UV-vis, diode-array, thermal conductivity, atomic adsorption, and FID's. In an example embodiment detection of these modified analytes can indicate the characteristics of the sample, referred to as sample characteristics. In one embodiment, sample characteristics can be acquired and correlated with respective ones of different values of an analytical parameter used to acquire the characteristic (e.g., ionization energy applied to the sample, waveform used for mass separation, analyte acquisition parameters of assembly 30). At least one sample characteristic that can be recorded includes total ion current in one embodiment.

In one embodiment, the progression of analysis including mass spectrometry analysis from sample inlet component 12 through component 14 can be controlled and/or monitored by processing circuitry of component 16 in the described exemplary embodiment. The processing circuitry may be implemented as a processor or other structure configured to execute executable instructions including, for example, software and/or firmware instructions. Other exemplary embodiments of processing circuitry 50 include hardware logic, PGA, FPGA, ASIC, and/or other structures. These examples of processing circuitry 50 are for illustration and other configurations are possible.

The processing circuitry can be configured to control the values of analytical component parameters described above and monitor component 14. Control of the analytical component parameter values by the processing circuitry can include, for example, dictating a predefined application of configurations of component 12 in combination with analysis parameters of component 14. In one embodiment, the processing circuitry can be configured to control the analyte modification component. In an example aspect, the processing circuitry can dictate a value of an analyte modification parameter during a first moment in time and a different analyte modification parameter during a second moment in time. Exemplary monitoring includes the recording of data received from the detection component. By varying analytical component parameter values utilized as described, sample characteristics can be obtained and associated with the parameter values and provided in the form of respective data sets according to the different values.

In one aspect the processing circuitry may execute data acquisition and searching programming and be configured to perform data acquisition and searching that includes the acquisition of sample characteristics such as total ion current or mass spectra. In another aspect, the processing circuitry can be configured to associate detected sample characteristics such as total ion current responsive to one or more analytical parameters such as an ionization parameter including electron impact ion source energy. The processing circuitry can be configured to monitor the detection component and associate detection of first analytes with a first sample characteristic and detection of second analytes with a second sample characteristic. The processing circuitry may also be configured to associate both the first sample characteristic with the first value of the analytical parameter, and the second sample characteristic with the second value of the analytical parameter. In an exemplary embodiment the processing circuitry can be configured to correlate both the first value of analyte modification parameter provided from the analyte modification component with the analytes detected during the first moment in time, and the second value of the analyte modification parameter provided from the analyte modification component with the analytes detected during the second moment in time. The processing circuitry can also be configured to prepare a sample data set that may include first and second data sets corresponding to the respective values.

In compliance with the statute, embodiments of the invention have been described in language more or less specific as to structural and methodical features. It is to be understood, however, that the entire invention is not limited to the specific features and/or embodiments shown and/or described, since the disclosed embodiments comprise forms of putting the invention into effect. The invention is, therefore, claimed in any of its forms or modifications within the proper scope of the appended claims appropriately interpreted in accordance with the doctrine of equivalents.

The invention claimed is:

1. A continuous air sampling instrumental analysis method, the method comprising:
providing carrier gas to a gas chromatograph head pressure controller, the head pressure controller being in fluid communication via a conduit with a gas chromatography column;
continuously flowing air sample from an air sampling port through a first heater manifold to a port valve configured to continuously provide the air sample through a second manifold and then, in a first position of the port valve, to a first sample capturing assembly or, in a second position of the port valve, to a second sample capturing assembly, wherein both sample capturing assemblies contain the same solid phase absorbent material and the port valve is operable between at least the two positions;
while the port valve is in the first position and the air sample is being provided to the first sample capturing assembly to capture gaseous analytes of the air sample, providing the carrier gas from the head pressure controller to the second sample capturing assembly and desorbing the second sample capturing assembly with the carrier gas to produce a first gaseous analyte stream comprising the carrier gas and providing the first gaseous analyte stream to the gas chromatography column;
while the port valve is in the second position and the air sample is being provided to the second sample capturing assembly to capture gaseous analytes of the air sample, providing the carrier gas from the head pressure controller to the first sample capturing assembly and desorbing the first sample capturing assembly with the carrier gas to produce a second gaseous analyte stream comprising the carrier gas and providing the second gaseous analyte stream to the gas chromatography column; and
flowing carrier gas from the head pressure controller through the first or second sample capturing assembly and the second manifold and then, in a third or fourth position of the port valve, to a vent line to precondition the first or second sample capturing assembly while the head pressure controller is also in fluid communication with and providing carrier gas to, the gas chromatography column while maintaining head pressure on the gas chromatography column.

2. The method of claim 1 wherein the gas chromatography column is operatively coupled to an analyte modification component.

3. The method of claim 1 further comprising performing cycles of analysis of the first and second gaseous analyte streams.

* * * * *